United States Patent
Thullier et al.

(10) Patent No.: US 8,344,109 B2
(45) Date of Patent: Jan. 1, 2013

(54) ANTI-RICIN ANTIBODY

(75) Inventors: Philippe Thullier, Bernin (FR); Michael Hust, Hannover (DE); Stefan Dubel, Braunschweig (DE)

(73) Assignees: Etat Francais Represente par le Delegue General pour l'Armement, Armees (FR); Technische Universitat Braunschweig-Institut fur Biochemie und Biotechnologie, Braunschweig (FR)

( * ) Notice: Subject to any disclaimer, the term of this patent is extended or adjusted under 35 U.S.C. 154(b) by 0 days.

(21) Appl. No.: 12/682,208

(22) PCT Filed: Oct. 10, 2008

(86) PCT No.: PCT/FR2008/051850
§ 371 (c)(1),
(2), (4) Date: Jul. 14, 2010

(87) PCT Pub. No.: WO2009/053637
PCT Pub. Date: Apr. 30, 2009

(65) Prior Publication Data
US 2011/0182878 A1    Jul. 28, 2011

(30) Foreign Application Priority Data
Oct. 11, 2007  (FR) ..................................... 07 07132

(51) Int. Cl.
*C07K 16/00* (2006.01)
*C07K 16/46* (2006.01)
*A61K 39/00* (2006.01)

(52) U.S. Cl. ................ 530/387.1; 530/387.3; 424/133.1

(58) Field of Classification Search ........................ None
See application file for complete search history.

(56) References Cited

U.S. PATENT DOCUMENTS
5,626,844 A    5/1997 Lemley et al.

FOREIGN PATENT DOCUMENTS
WO    WO 2005/020891         3/2005
WO    WO 2007/067780 A2 *    6/2007

OTHER PUBLICATIONS

SEQ ID No. 93 search printout.*
Beiboer et al., "Guided selection of a pan carcinoma specific antibody reveals similar binding characteristics yet structural divergence between the original murine antibody and its human equivalent" J. Mol Biol. (2000) 296: pp. 833-849.*
Brown et al. "Tolerance to Single, but not multiple, amino acid replacements in antibody VH CDR2" J. Immuno, 1996, 156: pp. 3285-3291.*
Eduardo Padlan, "Anatomy of the antibody molecule" Molecular Immun. 31(3) (1994), pp. 169-217.*
Klimka et al., "Human anti-CD30 recombinant antibodies by duided phage antibody selection using cell panning" British Journal of Cancer (2000) 83: pp. 252-260.*
William E. Paul, M.D. "Fundamental Immunology" 3rd Edition, 1993, 292-295.*
Rudikoff et al. "Single amino acid substitution altering antigen-binding specificity" Proc. Natl. Acad. Sci. USA, 79 (Mar. 1982), pp. 1979-1983.*
Vajdos et al. "Comprehensive functional maps of the antigen-binding site of an anti-ErbB2 antibody obtained with shotgun scanning mutagenesis" J. Mol. Biol. (2002) 320, pp. 415-428.*
Almagro, J.C. et al., Abstract of "Humanization of antibodies," Front Biosci., vol. 13 (2008) pp. 1619-1633.
Goldman, E.R. et al., "Facile Generation of Heat-Stable Antiviral and Antitoxin Single Domain Antibodies from a Semisynthetic Llama Library," Anal. Chem., vol. 78(24) (Dec. 15, 2006) pp. 8245-8255.
International Search Report dated Apr. 23, 2009 for Application No. PCT/FR2008/051850.
Laffly, E. et al., "Selection of a Macaque Fab with Framework Regions Like Those in Humans, High Affinity, and Ability to Neutralize the Protective Antigen (PA) of *Bacillus anthracis* by Binding to the Segment of PA between Residue 686 and 694," Antimicrobial Agents and Chemotherapy, vol. 49(8) (Aug. 2005) pp. 3414-3420.
Lemley, P.V. et al., "Identification and Characterization of a Monoclonal Antibody that Neutralizes Ricin Toxity in Vitro and in Vivo," Hybridoma, vol. 13(5) (Oct. 1994) pp. 417-421.
McGuinnes, C.R. et al., "Characterization of a Novel High-Affinity Monoclonal Immunoglobulin G Antibody against the Ricin B Subunit," Infection and Immunity, vol. 74(6) (Jun. 2006) pp. 3463-3470.
Wang, Y. et al., "Novel chimeric anti-ricin antibody C4C13 with neutralizing activity against ricin toxicity," Biotechnol. Lett., vol. 29(12) (Jul. 7, 2007) pp. 1811-1816.
Written Opinion dated Apr. 23, 2009 for Application No. PCT/FR2008/058150.

* cited by examiner

*Primary Examiner* — Maher Haddad
*Assistant Examiner* — James Rogers
(74) *Attorney, Agent, or Firm* — Frost Brown Todd LLC (57) ABSTRACT

The subject of the present invention is an anti-ricin antibody and the use thereof for the treatment of an individual suffering from ricin poisoning.

7 Claims, 1 Drawing Sheet

ANTI-RICIN ANTIBODY

The present invention relates to anti-ricin antibodies. In particular, the present invention relates to an anti-ricin antibody, directed against the A-chain of ricin.

Ricin is a toxin that is an inhibitor of protein synthesis, produced by a shrub of the family Euphorbiaceae, the castor-oil plant. Ricin is a very toxic glycoprotein with a molecular weight of about 60-65 kDa, which is formed from two polypeptide chains A and B, joined together by a disulfide bridge. The B-chain is a lectin which binds to glycoproteins containing galactose and to glycolipids expressed on the cell surface, facilitating the entry of ricin into the cytosol. The A-chain inhibits protein synthesis by irreversibly inactivating the 28S ribosomal subunit.

Ricin is toxic by the oral, parenteral, and pulmonary route. Ricin dispersed in the form of powder or aerosol can cause, after a period varying from a few minutes to several hours, signs of irritation of the eyes (burning sensation, lacrimation, conjunctivitis of varying severity) and of the pharynx as well as a varying degree of respiratory irritation: cough, dyspnoea, pulmonary edema, which can lead to acute respiratory distress syndrome. In humans, the estimated lethal dose of ricin is from 1 to 10 µg/kg.

A test for rapid diagnosis of ricin poisoning by the pulmonary route has recently been developed (Guglielmo-Viret et al. 2007).

Following exposure to ricin, the following antidotes can be used: analogs of sugar that prevent ricin binding to its target or inhibitors of the catalytic subunit such as azidothymidine.

Another strategy for the treatment of ricin poisoning is vaccination. For example, antibodies have been developed with the aim of interfering with the binding of the toxin of anthrax to the cell surface receptors or with the aim of inhibiting assembly of the toxin. At present, however, no specific therapy is available for ricin. Just one chimeric antibody has been developed by Wang et al. (Wang et al., 2007, Biotechnol Lett 29:1811-1816). This chimeric antibody is derived from the murine antibody c4C13. This antibody belongs to the first generation of recombinant antibodies, and is known to induce secondary effects (HACA "human anti chimeric antibody") and low tolerance.

Passive immunization with antibodies is still, however, an effective strategy for neutralizing ricin. The development of new antibodies for neutralizing ricin is thus of general interest for the prevention and effective treatment of ricin poisoning.

In a recent work, the inventors immunized a macaque with the A-chain of ricin to obtain antibodies intended for treating human infection with ricin. Starting from bone marrow, the inventors amplified the genes coding for fragments of specific antibodies of the A-chain of ricin and cloned them to obtain a library. The library was then screened to isolate fragments of antibodies with strong affinity and that are strongly neutralizing.

The inventors were thus able to isolate a fragment scFv with strong affinity and that is strongly neutralizing, designated 43RCA. The advantage of such an antibody is that these framework regions notably display strong sequence identity with framework regions of human antibodies, and with framework regions encoded by human germline genes.

Therefore one object of the present invention is to supply an anti-ricin antibody, directed against the A-chain of ricin.

The present invention also relates to a composition comprising said anti-ricin antibody as well as a pharmaceutical composition comprising said anti-ricin antibody and a pharmaceutically acceptable vehicle.

The present invention also relates to the use of said modified antibody for the preparation of a pharmaceutical composition intended for the treatment or prevention of ricin poisoning.

The present invention also relates to a kit for the detection of ricin, comprising said anti-ricin antibody as well as a method of detection of ricin.

The present invention will be better understood on the basis of the following definitions.

The term "antibody" refers to an immunoglobulin molecule or a fragment of an immunoglobulin molecule having the capacity to bind specifically to a particular antigen. An antibody according to the present invention can be a whole antibody (chimeric antibody, humanized antibody, in particular) or an antibody fragment F(ab')$_2$, Fab, scFv, Fv, single-chain antibody in particular.

The term "ricin" refers to any disease caused, directly or indirectly, by ricin poisoning. Ricin does not display any selectivity for cells of a specific type. Since all types of cells can be affected, the symptoms depend on the site of entry of the toxin into the human body. Depending on the dose, the first symptoms appear after a latency period of 2 to 24 h. After inhalation of a large dose of ricin, the victim may present general symptoms (fever, sweating, nausea) and respiratory difficulties, even including pulmonary edema. Disorders of gas exchange can lead to death. After oral ingestion of ricin, the victim suffers from vomiting and diarrhea, which can become bloody, leading to severe dehydration or even collapse. Within a few days, the functions of the spleen, liver and kidneys can have deteriorated considerably. Death due to ricin poisoning can occur in 36 to 72 h after intoxication, depending on the dose of ricin and the route of intoxication.

The term "isolated" means "amplified in vitro by PCR", "produced recombinantly by cloning", "purified by gel separation or by cleavage", or "synthesized for example by chemical synthesis".

The term "vector" refers to a nucleic acid in which the sequences of interest can be inserted by restriction and then ligation for transport between different genetic environments or for expression in a host cell. The vectors are for example plasmids, cosmids, yeast artificial chromosomes (YAC), bacterial artificial chromosomes (BAC) and artificial chromosomes derived from bacteriophage P1 (PAC), vectors derived from viruses. A cloning vector is a vector capable of replicating in a host cell and which is moreover characterized by the presence of one or more restriction sites for endonucleases. An expression vector is a vector in which the DNA sequence of interest can be inserted by restriction or ligation in such a way that it can be replicated and/or transcribed to RNA. The vectors can additionally contain one or more markers for selection or identification of the cells that have been transformed or transfected with the vector.

The term "humanized antibody" refers to antibodies of animal origin in which human components have been substituted for certain original components.

The term "prevention of a disease" corresponds to the prevention of the development of said disease in a subject, in particular a human, in whom the disease has not yet appeared.

The term "treatment of a disease" corresponds to the inhibition of said disease, i.e. the stopping of its development, its regression, or the disappearance of the symptoms and/or consequences of the disease, or the disappearance of the causes of the disease.

The term "therapeutically effective amount" refers to the amount that is sufficient to effect the treatment when it is administered to a subject requiring said treatment. The therapeutically effective amount depends on the subject, the stage of the disease to be treated and the method of administration, and can be determined by routine procedures by a person skilled in the art.

As is well known, only a part of the antibody, the variable region, is involved in the binding of the antibody to its epitope. The constant regions of the antibody activate the immune effectors, notably phagocytes, killer cells and complement, as well as other receptors such as the Brambell receptor that is involved in the biological recycling of antibodies; these constant regions are not involved in binding to the antigen. An antibody whose constant region (Fc) has been cleaved enzymatically so as to preserve its hinge region is designated as an F(ab')2 fragment and conserves the two binding sites to the antigen.

Similarly, an antibody whose constant region, including the hinge region, has been enzymatically cleaved, or which was produced without this region, is designated as a Fab fragment and conserves one of the two binding sites to the antigen. The Fab fragments consist of a light chain which is bound covalently to a portion of the heavy chain called Fd.

A fragment scFv consists of the variable region of the heavy chain and the variable region of the light chain joined together by a peptide bond, which enables the two variable regions to combine to form a binding site to the antigen.

In the variable region there are the regions that determine the complementarity (CDRs, complementarity determining regions), also called hypervariable regions, which interact directly with the antigen. Modifying the CDRs can therefore make it possible to modify the affinity of an antibody. In the variable region, there are regions of a second type, called framework regions (FRs), which maintain the tertiary structure of the CDRs. These framework regions are fairly specific to the species in which the antibody was produced. Thus, in the variable regions of the heavy chain and in the light chain, there are four framework regions (FR1 to 4) separated respectively by three CDRs (CDR1 to 3). These FR and CDR regions are arranged from the N-terminal domain to the C-terminal domain in the following order: FR1, CDR1, FR2, CDR2, FR3, CDR3, FR4. The CDR3 regions belonging to the variable regions of the heavy chain and of the chain are particularly important for recognition of the antigen.

The inventors identified a fragment scFv, for which the variable region of the heavy chain has the sequence SEQ ID No. 1 and the variable region of the light chain has the sequence SEQ ID No. 2.

This fragment scFv displays strong affinity equal to $5\,10^{-11}$ M and possesses a strong potential for neutralization of ricin.

The present invention relates to an anti-ricin antibody, characterized in that the CDR3 region of the variable region of the heavy chain has the sequence SEQ ID No. 3, and/or the CDR3 region of the variable region of the light chain has the sequence SEQ ID No. 4.

In a preferred embodiment of the invention, the anti-ricin antibody is characterized in that the CDR3 region of the variable region of the heavy chain has the sequence SEQ ID No. 3 and the CDR3 region of the variable region of the light chain has the sequence SEQ ID No. 4.

According to a first embodiment of the invention, the anti-ricin antibody is characterized in that the variable region of the heavy chain additionally comprises the regions CDR1 and/or CDR2 having respectively the sequences SEQ ID No. 5 and SEQ ID No. 7.

According to a second embodiment of the invention, the anti-ricin antibody is characterized in that the variable region of the light chain additionally comprises the regions CDR1 and/or CDR2 having respectively the sequences SEQ ID No. 6 and SEQ ID No. 8.

In a preferred embodiment of the invention, the anti-ricin antibody is characterized in that the variable region of the heavy chain comprises the regions CDR1, CDR2 and CDR3 having respectively the sequences SEQ ID No. 5, SEQ ID No. 7 and SEQ ID No. 3, and the variable region of the light chain comprises the regions CDR1, CDR2 and CDR3 having respectively the sequences SEQ ID No. 6, SEQ ID No. 8 and SEQ ID No. 4.

According to an even more preferred embodiment of the invention, the anti-ricin antibody is characterized in that the variable region of the heavy chain has the amino acid sequence represented by SEQ ID No. 1 and the variable region of the light chain has the amino acid sequence represented by SEQ ID No. 2.

The present invention also relates to a fragment scFv, comprising the sequence SEQ ID No. 1 and the sequence SEQ ID No. 2 joined together by a peptide bond such as the bond $(G_4S)x3$ or the bond ASTKGPKLEEGEFSEARV (SEQ ID No. 10).

Figure 1:
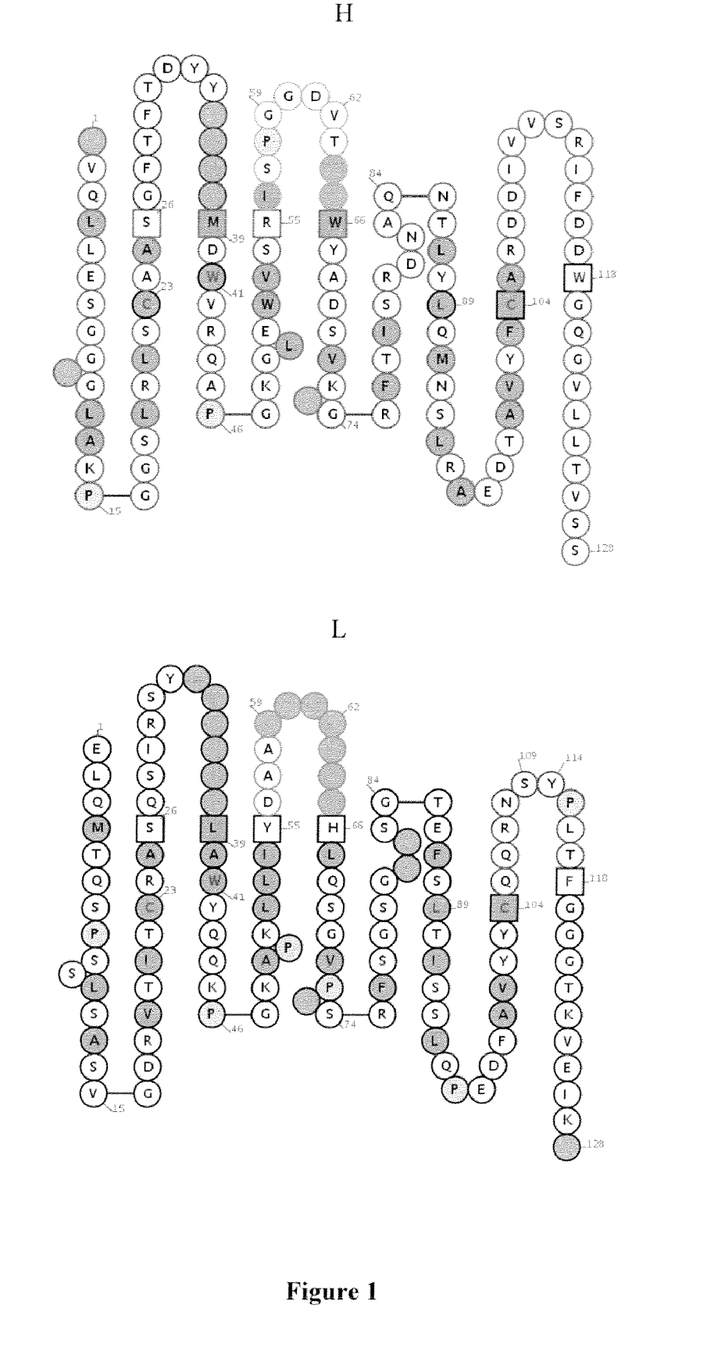
FIG. 1: string-of-pearls diagram of the variable region of the heavy chain and of the variable region of the light chain of the anti-ricin antibody.

The sequences SEQ ID No. 1 and SEQ ID No. 2 are presented in the form of a two-dimensional diagram in FIG. 1. The DNA sequences coding for these sequences SEQ ID No. 1 and SEQ ID No. 2 correspond respectively to FJ178346 and FJ178347.

The present invention also relates to an scFv anti-ricin fragment having the sequence SEQ ID No. 9.

The affinity $K_D$ of an antibody can be measured by the conventional techniques known by a person skilled in the art. The affinity constant of the anti-ricin antibody of the present invention was calculated from the association and dissociation constants measured in real time by surface plasmon resonance, as explained in the examples.

The present invention therefore supplies fragments F(ab')2, Fab, Fv, scFv and Fd of an anti-ricin antibody as described above. Said fragments also include CDRs and peptides whose sequence is a portion of the antibody, in particular of its CDRs, of its variable domains or a combination of thereof.

The present invention also supplies chimeric antibodies in which the part Fc and/or the constant regions of the fragment Fd and of the light chain of the antibody are derived from human or nonhuman homologous sequences.

According to one embodiment of the invention, the part Fc of the antibody can be selected so as to produce IgAs, IgMs or IgGs.

According to another embodiment of the invention, the part Fc of the antibody can be a part Fc derived from mice, horses, sheep, cattle or other mammals.

The present invention also supplies fragments scFv fused to regions Fc.

According to a preferred embodiment of the invention, the anti-ricin antibody according to the invention possesses a part Fc of human origin. These complete antibodies are preferred for administration in humans as they have a longer half-life than antibody fragments such as Fab fragments, and are more suitable for intravenous, intraperitoneal, intramuscular, subcutaneous, transdermal or aerosol administration.

In certain embodiments of the invention, the Fab or scFv fragments are preferred for the following reasons: a) as the Fab or scFv fragments only have a single binding site to the antigen, immune complexes of large size cannot form, b) the absence of a region Fc prevents the appearance of an inflammatory reaction activated by Fc, such as the complement activation cascade, c) it is easier for a small molecule Fab or scFv to penetrate into the tissues, and d) Fab or scFv is easily produced at low cost in bacteria such as *E. coli*.

Thus, one object of the present invention is to supply Fabs of the anti-ricin antibody according to the invention, fragments of this antibody that are smaller or larger than Fab fragments or alternatively epitope binding peptides, and in particular peptides derived from the hypervariable regions of the anti-ricin antibody according to the invention.

In particular, the present invention relates to peptides derived from the regions CDR3 having the sequence SEQ ID No. 3 or SEQ ID No. 4.

Another object of the invention is to supply variants of the anti-ricin antibody of the present invention.

"Variant of the anti-ricin antibody of the present invention" means any variant that has conserved the ability to bind to ricin A. This ability to bind to ricin A can be determined by conventional techniques that are well known by a person skilled in the art, for example ELISA or Western-blot.

Variants of the amino acid sequence of the antibody of the present invention can be prepared using just one portion of the nucleotide or peptide sequences described in the present text. These variants comprise for example deletions and/or insertions and/or substitutions of residues in the amino acid sequence of the antibody. The present invention relates to any variant obtained from the sequences presented in this text since the expression of the final construct possesses the characteristics expected of an anti-ricin antibody. Changes of amino acids can also alter the post-translational process of the antibody, for example the number or the position of the glycosylation sites.

The nucleic acid sequences coding for the amino acid sequences of the variants of the antibody of the present invention can be prepared by conventional methods, for example gene synthesis, or directed mutagenesis or random mutagenesis followed by a stage of selection of the products obtained.

To analyze the consequences of a mutation at a given site, the variants must be tested for the desired activity. In general, the amino acid sequence of the variants of the antibody of the present invention has at least 70% sequence identity with the original sequence of the variable region of the anti-ricin antibody, preferably at least 75%, 80%, 85%, 90% and more preferably 95% sequence identity with the original sequence of the variable region of the anti-ricin antibody.

Sequence identity is defined here as the percentage of amino acids in the sequence of the variant that are identical to those of the original sequence, after aligning the sequences and introducing spaces, if necessary, to obtain the maximum of sequence identity, and without regarding the conservative substitutions (Table 1) as forming parts of the sequence identity.

The sequence identity can be determined by the standard methods using programs such as BLAST or FASTA.

Examples of variants are as follows:

Variants Obtained by Insertion

The insertion of amino acids comprises the N or C-terminal fusions ranging from one residue to polypeptides comprising more than 100 residues, as well as insertions of one or more amino acids within the sequence. Examples of terminal insertions are an antibody with an N-terminal methionine residue or an antibody fused with a marker epitope (HA, c-myc, polyhistidine sequence, D glycoprotein of HSV) or an antibody fused to a polypeptide that increases the half-life of the antibody.

Variants Obtained by Substitutions

These variants are obtained for example by substitution mutagenesis in the hypervariable or framework regions of the antibody. The conservative substitutions are shown in Table 1.

| Original amino acid | Possible substitutions | Preferred substitutions |
|---|---|---|
| Ala (A) | val; leu; ile | val |
| Arg (R) | lys; gln; asn | lys |
| Asn (N) | gln; his; asp; lys; gln | arg |
| Asp (D) | glu; asn | glu |
| Cys (C) | ser; ala | ser |
| Gln (Q) | asn; ala | ser |
| Glu (E) | asp; gln | asp |
| Gly (G) | ala | |
| His (H) | asn; gln; lys; arg | |
| Ile (I) | leu; val; met; ala; phe | leu norleucine |
| Leu (L) | norleucine; ile; val met; ala; phe | ile |
| Lys (K) | arg; gln; asn | arg |
| Met (M) | leu; phe; ile | leu |
| Phe (F) | leu; val; ile; ala; tyr | |
| Pro (P) | ala | |
| Ser (S) | thr | |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications of the biological properties of the antibody of the present invention can be obtained by selection of substitutions that differ significantly in their effect on maintaining (a) the structure of the polypeptide backbone at the level of the substitution, (b) the charge or the hydrophobicity of the molecule at the target site, or (c) the volume of the side chain.

The natural residues can be divided into different groups according to their properties:

(1) hydrophobic residues: norleucine, met, ala, val, leu, ile;
(2) hydrophilic neutral residues: cys, ser, thr;
(3) acid residues: asp, glu;
(4) basic residues: asn, gln, his, lys, arg;
(5) residues influencing the orientation of the chain: gly, pro; and
(6) aromatic residues: trp, tyr, phe.

Conservative substitutions involve replacing an amino acid with another member of the same group, whereas nonconservative substitutions involve replacing one of the groups with a member of another group.

Any cysteine residue not involved in maintaining the conformation of the antibody can also be substituted, generally with a serine, to increase the oxidative stability of the molecule. Moreover, cysteine bonds can be added to increase the stability of the antibody (in particular in the case of fragment Fv).

Variants Obtained by Affinity Maturation

Affinity maturation involves the preparation and screening of antibody variants that possess mutations (deletions, insertions, or substitutions) in the variable regions of the parent antibody, as well as the selection of variants having improved biological properties such as better binding affinity relative to the parent antibody or better tolerance when administered in humans. A conventional method of generating said variants with improved affinity is affinity maturation using the techniques of mutagenesis followed by selection, for example by "phage display".

One object of the present invention is also to supply an anti-ricin antibody according to the invention that is better tolerated by the human immune system. Said humanized antibody has the advantage of not inducing, or inducing less, immune response against itself, and of having a longer half-life.

The invention relates to an anti-ricin antibody according to the invention that has been humanized. This anti-ricin antibody according to the invention can be humanized or super-humanized by any technique known by a person skilled in the art. Techniques of humanization that aim to increase the homology of the framework regions of the antibody with framework regions encoded by human somatic genes coding for antibodies, are for example described in the review by Almagro et al. "Humanization of antibodies" (Almagro et al., 2008, Front. Biosci. January 1; 13:1619-33). Techniques derived from humanization, and called super-humanization, have also been described: they can also aim to increase the homology of the framework regions of the antibody with framework regions encoded by human germline genes coding for antibodies. These techniques have in common that they succeed in preserving the affinity of the antibody for its antigen, whereas the sequences of the framework regions of this antibody were modified to increase the degree of similarity with their human homologs.

In one embodiment, a humanized anti-ricin antibody according to the invention additionally comprises at least one mutation in the variable region of the heavy chain selected from the group comprising: none/Q (1), L/V (5), A/V (13), D/S (40), V/I (42), R/Y (55), W/Y (66), Q/K (84), T/S (86), F/Y (103), V/T (122), L/V (124).

The mutation none/Q (1) means that an amino acid Q (glutamine) is added in position 1. The mutation L/V (5) means that the amino acid V (valine) replaces the amino acid L (leucine) in position 5. The positioning of the amino acids is shown in FIG. 1.

When the positioning of the amino acids is calculated from SEQ ID NO: 1, the anti-ricin antibody according to the invention is humanized by additionally comprising at least one mutation in the variable region of the heavy chain selected from none/Q (1), L/V (5), A/V (12), D/S (35), V/I (37), Y/R (50), W/Y (59), Q/K (76), T/S (78), F/Y (95), V/T (114), L/V (116).

In another embodiment of the invention, the humanized anti-ricin antibody according to the invention additionally comprises at least one mutation in the variable region of the light chain selected from the group comprising: E/D (1), L/I (2), M/L (4), S/F (10), H/T (66), S/T (88), V/T (101).

The positioning of the amino acids is shown in FIG. 1.

When the positioning of the amino acids is calculated from SEQ ID NO: 2, the anti-ricin antibody according to the invention is humanized by additionally comprising at least one mutation in the variable region of the light chain selected from E/D (1), L/I (2), M/L (4), S/F (10), H/T (53), S/T (72), V/T (85).

In another embodiment, the humanized anti-ricin antibody according to the invention additionally comprises at least one mutation in the variable region of the light chain selected from the group comprising: E/D(1), L/I(2), S/T(10), H/S(66), Q/E(68), S/T(88), E/D(97), V/T(101). The positioning of the amino acids is shown in FIG. 1.

When the positioning of the amino acids is calculated from SEQ ID NO: 2, the anti-ricin antibody according to the invention is humanized by additionally comprising at least one mutation in the variable region of the light chain selected from: E/D(1), L/I(2), S/T(10), H/S(53), Q/E(55), S/T(72), E/D(81), V/T(85).

In a preferred embodiment of the invention, the humanized anti-ricin antibody according to the invention additionally comprises at least one mutation in the variable region of the heavy chain as described above and at least one mutation in the variable region of the light chain as described above.

Based on the above description the amino acid sequences of the variable region of the heavy chain and of the variable region of the light chain of the anti-ricin antibodies according to the invention, a person skilled in the art is able to synthesize, or cause to be synthesized, nucleic acids that code for these amino acid sequences.

The present invention therefore relates to a nucleic acid coding for an anti-ricin antibody according to the invention.

The present invention also relates to a vector comprising said nucleic acid.

These nucleic acids can be comprised in a recombinant vector for cloning or for expression of the antibodies of the invention.

The present invention includes all the recombinant vectors containing coding sequences for eukaryotic or prokaryotic transformation, transfection or gene therapy. Said vectors can be prepared according to the conventional techniques of molecular biology and will additionally comprise a suitable promoter, optionally a signal sequence for export or secretion, and regulatory sequences necessary for the transcription of the nucleotide sequence.

A fusion polypeptide can be used for purification of the antibodies of the present invention. The fusion domain can for example include a polyhistidine tail, which permits purification on Ni+ columns, or a filamentous phage membrane anchor which is particularly useful for gene library screening based on phage display technology.

One of the vectors that is suitable within the scope of the invention is a molecule of recombinant DNA adapted for receiving and expressing a first and a second DNA sequence, so as to permit the expression of a heterodimeric antibody such as a full-length antibody or F(ab')2 or Fab fragments according to the invention. Such a vector offers a system for independently cloning the two DNA sequences in two separate cassettes present in the vector, so as to form two separate cistrons for expressing a first and a second polypeptide of the heterodimeric antibody. Such an expression vector is called a di-cistronic vector.

The modified antibodies of the present invention can be produced in eukaryotic cells such as CHO or human or murine hybridomas for example, as well as in plant cells.

The present invention also relates to prokaryotic or eukaryotic host cells, comprising a vector according to the invention.

Another object of the present invention is to supply a composition comprising at least one anti-ricin antibody according to the invention.

The present invention also relates to a pharmaceutical composition comprising at least one anti-ricin antibody according to the invention and at least one pharmaceutically acceptable vehicle. Said vehicle corresponds in the sense of the invention to a nontoxic material that does not interfere with the effectiveness of the biological activity of the active ingredients of the composition. The term "pharmaceutically acceptable" refers to a nontoxic material that is compatible with a biological system such as a cell, a cell culture, a tissue or an organism. The characteristics of the vehicle will depend on the method of administration.

The present invention also relates to a vaccine or a medicinal product comprising at least one anti-ricin antibody according to the invention.

The present invention relates to the use of at least one anti-ricin antibody according to the invention for the preparation of a pharmaceutical composition, a medicinal product or a vaccine intended for the treatment or prevention of ricin poisoning.

The anti-ricin antibody according to the invention can be labeled. Examples of markers include enzymes, radioisotopes, fluorescent compounds, colloidal metals, chemiluminescent compounds, and bioluminescent compounds. The methods of binding a marker to an antibody are well known by a person skilled in the art.

Another labeling technique consists of coupling the antibody to haptens of low molecular weight, and said haptens can be specifically modified by means of a second reaction. Examples of haptens are biotin, which reacts with avidin, or dinitrophenol, pyridoxal or fluorescein, which can react with specific antihapten antibodies.

One object of the present invention is to supply a kit for detecting the A-chain of ricin. This kit comprises:
 a container comprising at least one anti-ricin antibody according to the invention, which can be labeled or not,
 optionally, a container comprising buffer solutions
 and optionally a container comprising means for detecting said labeled anti-ricin antibody, such as a protein for binding to biotin, for example avidin or streptavidin, bound to a reporter molecule, such as a fluorescent or enzymatic marker. This container can also comprise means for detecting said nonlabeled anti-ricin antibody, i.e. essentially antibodies or antibody fragments.

The anti-ricin antibody of the invention can be used in vitro, for example in immunoassays in which they are used in the liquid phase or bound to a carrier of solid phase. Examples of well-known carriers are glass, polystyrene, polypropylene, polyethylene, dextran, nylon, amylase, natural or modified cellulose, polyacrylamide, agarose or magnetite. Examples of immunologic tests using the anti PA antibody of the invention are radioimmunoassays, histoimmunological labeling, ELISA, Western blots, immunoprecipitation assays, immunodiffusion assays, complement binding assays, FACS analyses or analyses using protein chips.

The present invention relates to supplying a method of in-vitro detection of the A-chain of ricin in a biological sample, comprising:
 contacting the sample with at least one anti-ricin antibody according to the invention, and
 detecting said anti-ricin antibody as an indicator of the presence of said ricin.

The biological sample can be liquid: for example saliva, urine, cerebrospinal fluid, serum or blood, or solid or semisolid, for example tissues or fecal matter or a solid tissue such as commonly used in histological diagnostics.

The present invention also relates to supplying a method of in-vivo detection of the A-chain of ricin, in which a labeled anti-ricin antibody according to the present invention is administered to a subject. The amount of labeled antibody administered must be sufficient to permit detection of the binding of the antibody to the toxin. The amount of labeled antibody administered will depend on factors such as the subject's age and sex, as well as the stage of the disease. The amount administered can vary between 0.01 mg/kg and 50 mg/kg, preferably between 0.1 mg/kg and 20 mg/kg, and more preferably between 0.1 mg/kg and 2 mg/kg.

For carrying out the diagnosis in vivo, the anti-ricin antibody of the invention must be bound to a radioisotope directly, or indirectly via functional groups. Functional groups commonly used are for example diethylenetriaminepentaacetic acid (DTPA) and ethylenediaminetetraacetic acid (EDTA). Examples of radioisotopic metal ions are $^{111}$In, $^{97}$Ru, $^{67}$Ga, $^{68}$Ga, $^{72}$As, $^{89}$Zr and $^{201}$Tl.

The anti-ricin antibody of the invention can also be labeled with a paramagnetic isotope for diagnosis by magnetic resonance imaging (MRI) or by electron spin resonance (ESR). Positron-emitting gamma radioisotopes can also be used, such as $^{157}$Gd, $^{55}$Mn, $^{162}$Dy, $^{68}$Ga, $^{52}$Cr, and $^{56}$Fe.

The anti-ricin antibody of the invention can also be used in vitro or in vivo for monitoring the development of the treatment of the disease, for example by determining the increase or decrease in the number of cells targeted by the ricin or the changes in the concentration of ricin in a biological sample.

The present invention relates to a method of treatment of a subject, preferably a human, possibly poisoned with ricin, in which a therapeutically effective amount of an anti-ricin antibody according to the invention is administered to said subject.

A therapeutically effective amount corresponds to a sufficient amount for reducing the symptoms of the disease and the development of the infection. This amount can vary with the subject's age and sex, and the stage of the disease, and will be determined by a person skilled in the art. A therapeutically effective amount can vary between 0.01 mg/kg and 50 mg/kg, preferably between 0.1 mg/kg and 20 mg/kg, and more preferably between 0.1 mg/kg and 2 mg/kg, in one or more daily doses, for one or more days.

The method of administration can be by injection or by gradual infusion. The injection can be intravenous, intraperitoneal, intramuscular, subcutaneous or transdermal. Another possible method of administration is by aerosol. The preparations for parenteral administration can include aqueous or nonaqueous sterile solutions, suspensions or emulsions. Examples of nonaqueous solvents are propylene glycol, polyethylene glycol, vegetable oils, such as oil olive, or injectable organic esters such as ethyl oleate.

Aqueous vehicles comprise water, alcohol/water solutions, emulsions or suspensions.

The present invention also relates to an immunoconjugate comprising an anti-ricin antibody according to the invention, bound directly or indirectly to a therapeutic agent.

Said therapeutic agents comprise chemical agents, radionuclides, immunotherapeutic agents, cytokines, chemokines, toxins or enzyme inhibitors. Examples of toxins are the A-chain of diphtheria, the A-chain of exotoxin, the A-chain of abrin, the A-chain of modeccin, alpha-sarcin, Aleurites fordii proteins, dianthin proteins, Phytolacca americana proteins, momordica charantia inhibitor, curcin, crotin, sapaonaria officinalis inhibitor, gelonin, mitogellin, restrictocin, phenomycin, enomycin and tricothecenes. Examples of radionuclides are $^{212}$Bi, $^{131}$I, $^{131}$In, $^{90}$Y, and $^{186}$Re.

The present invention will be better understood from the following additional description, which refers to an example of production of the anti-ricin antibody according to the invention.

In the examples that follow, which are given for purposes of illustration, reference will be made to the appended drawing.

The IMGT string-of-pearls representation is based on the IMGT numbering.

Materials and Methods

*E. coli* Strains

The following *E. coli* strains were used:
 XL1 (Stratagene, La Jolla, Calif.): recA1, endA1, gyrA96 thi-1 hsdR17 sup E44 relA1 lac [F'proAB lacIqZΔM15 Tn10(Tetr)]
 SURE (Stratagene): e14(McrA) Δ(mcrCB-hsdSMR-mrr) 171 endA1 supE44 thi-1 gyrA96 relA1 lac recB recJ sbcC umuC::Tn5 (Kanr) uvrC [F' proAB lacIqZΔM15 Tn10 (Tetr)]-HB2151, used for the expression of soluble scFvs.

Toxins

The A-chain of ricin, injected in the macaque, was purchased from Vector Labs, as was the complete ricin.

Construction of the Library of Anti-Ricin Antibodies

A macaque (*Macaca fascicularis*) was anesthetized (0.8 ml of Imalgene®, Merial, Lyons, France) and 5-ml bone marrow samples were taken before the first and the last injection (Day 0) of A-chain of ricin, carried out for the purpose of immunizing the animal. Moreover, samples were taken regularly after D0 and for a month. The RNA of these bone marrow samples was isolated using Trizol® (Euromedex, France) and the single-stranded cDNA was generated using the Superscript preamplification system (Invitrogen, Cergy Pontoise, France) in the presence of random oligoTs.

Amplification by polymerase chain reaction (PCR) was carried out in the same conditions as described in Glamann and Hirsch, 2000 with the nine combinations of IgH primers and the seven combinations of IgK primers, so as to generate the PCR products H and L respectively.

The PCR products H and L were first inserted into the pGemT vector (Promega, Madison, Wis.) to construct a first sublibrary of DNA coding for the heavy chain (fragment Fd) and a second sublibrary of DNA coding for the light chain. The cDNA in pGEM was reamplified with sets of two oligonucleotide primers for the introduction of restriction sites. One set of kappa human and macaque oligonucleotide primer was used as oligonucleotide sense primers, and just one set specific to the macaque was used as oligonucleotide antisense primers (Table I).

Each PCR was performed using Taq Red (Sigma, Hamburg, Germany) for 20 cycles (30 s 94° C., 30 s 57° C., 30 s 72° C.). The PCR products were separated by agarose gel electrophoresis and then purified. The amplified PCR products VL or VH were grouped together. The library was constructed in two stages: the VL fragments were inserted into pHAL14, then the VH fragments were inserted into pHAL14 containing the VL set. The pHAL14 vector is derived from the pHAL1 phagemid vector.

HAL14 and the VL fragments were digested with MluI and NotI (NEB, Frankfurt, Germany), the enzymes were inactivated, pHAL14 was dephosphorylated using calf intestinal phosphatase (MBI Fermentas) and the DNA was purified. The PCR products VL were inserted into the dephosphorylated pHAL14 preparation. The DNA was precipitated from the reaction mixtures with ethanol and sodium acetate and the deposit was washed twice in 70% ethanol. The plasmids (library of the VL chain) were isolated using the Plasmid Midi kit (Qiagen, Hilden, Germany). The VL chain library and the VH fragments were digested with NcoI and IndIII (NEB), and binding and electroporation were then carried out as described for VL.

Selection of Antibodies by Phage

The particles of phages-scFv were purified and concentrated from 50 ml of culture by precipitation with PEG, then resuspended in 3 ml of 1% PBS-BSA-0.02% azide and filtered on a 0.45 µm filter. The titer of this phage preparation was about $5 \cdot 10^{10}$ pfu/ml. The phages-scFv were submitted to three cycles of infection-selection-recovery as described previously (Andris-Widhopf, Rader et al. 2000).

Expression of Soluble scFv, Periplasmic Extraction and Purification

Each DNA variant was transformed in bacteria of the *E. coli* strain called HB2151, made chemically competent. The cells were cultivated at 30° C., stirred at 250 rpm in 1 L of SB medium containing 50 µg/ml of carbenicillin and 0.1% of glucose. When the culture reached an $A_{600}$ of 1.5, induction with 1 mM of IPTG was carried out for 18 h at 22° C.

The scFvs were extracted with polymyxin B sulfate (Sigma) and were purified on a nickel column (Ni-NTA spin column, QIAGEN, Valencia, Calif.) according to the manufacturer's instructions, then dialyzed with PBS 1× at 4° C. for 3 h.

Quantification of the scFv

The purity of the Fab was tested by SDS-PAGE and its concentration was determined using the software Quantity One® (Biorad).

Real-Time Measurement of Surface Plasmon Resonance (SPR)

The constants of the kinetics of interaction between ricin and the scFv obtained previously were determined using the Biacore X SPR system (BIAcore, Uppsala, Sweden). The ricin was immobilized on a CM5 sensitive chip using an amine coupling procedure by injection of 30 µl of 2 µg/ml of ricin in 10 mM of sodium acetate pH 4.5. To minimize the probability of rebinding, $K_D$ was measured using a high flow rate (30 µl/min) and a minimal amount of coupled antigen (about 500 RU, resonance units). The extent of binding of different concentrations of scFv in the range from 5 to 400 nM in PBS was determined at a flow of 30 µl/min. The binding data were entered in a 1:1 Langmuir model of the BIA evaluation software. The association and dissociation constants ($k_{on}$ and $k_{off}$ respectively) for the binding of scFv to ricin were determined at 35° C.

Sequence Analysis

The sequences of the variable regions of the heavy and light chains of the selected clones were determined by Genome Express (Meylan, France) using the primers Mkmyc and MkpelB (Kirsch et al., 2005). The sequences were analyzed in line, using the IMGT system (http:/imgt.cines.fr).

Results

The inventors thus detected an anti-ricin scFv fragment, the fragment 43RCA according to the invention, whose affinity measured by surface plasmon resonance is equal to $5 \cdot 10^{-11}$ M.

Neutralization of ricin toxicity was then tested in the laboratory.

J774.2 cells, of the macrophage type, were cultured at a rate of 14000 cells per 200 µl well. Incubation of these cells for 24 h with 15 ng/ml of ricin leads to the death of 100% of the cells.

Co-incubation of the ricin with the various scFVs obtained from the library made it possible to investigate the neutralizing capacity of these antibody fragments.

The results of this neutralization test show that the 43RCA antibody fragment according to the invention neutralizes 50% of the toxicity at a concentration of 30 ng/ml ($IC_{50}$=30 ng/ml).

The invention claimed is:

1. An isolated anti-ricin antibody characterized in that the CDR3 region of the variable region of the heavy chain has the sequence SEQ ID NO: 3 or the CDR3 region of the variable region of the light chain has the sequence SEQ ID NO: 4, and wherein said anti-ricin antibody is a neutralizing antibody, and further, characterized in that the variable region of the heavy chain comprises the regions CDR1 and CDR2 having respectively the sequences SEQ ID NO: 5 AND SEQ ID NO: 7, and the variable region of the light chain comprises the regions CDR1 AND CDR2 having respectively the sequences SEQ ID NO: 6 AND SEQ ID NO: 8.

2. The isolated anti-ricin antibody as claimed in claim 1, characterized in that the variable region of the heavy chain has the amino acid sequence represented by SEQ ID NO: 1 and the variable region of the light chain has the amino acid sequence SEQ ID NO: 2.

3. An anti-ricin scFv having the sequence SEQ ID NO: 9.

4. A composition comprising at least one isolated antibody as claimed in claim 1 or 2.

5. A pharmaceutical composition comprising at least one isolated antibody as claimed in claim 1 or 2 and at least one pharmaceutically acceptable vehicle.

6. A kit for detecting the A-chain of ricin, said kit comprising:
 a container comprising at least one labeled antibody as claimed in claim 1 or 2, and
 a container comprising means for detecting said labeled antibody.

7. An immunoconjugate comprising an antibody as claimed in claim 1 or 2 bound to a therapeutic agent.

* * * * *

SEQUENCE LISTING

<160> NUMBER OF SEQ ID NOS: 10

<210> SEQ ID NO 1
<211> LENGTH: 119
<212> TYPE: PRT
<213> ORGANISM: Artificial Sequence
<220> FEATURE:

<223> OTHER INFORMATION: Macaca fascicularis

<400> SEQUENCE: 1

Val Gln Leu Leu Glu Ser Gly Gly Leu Ala Lys Pro Gly Gly Ser
1               5                   10                  15

Leu Arg Leu Ser Cys Ala Ala Ser Gly Phe Thr Phe Thr Asp Tyr Tyr
            20                  25                  30

Met Asp Trp Val Arg Gln Ala Pro Gly Lys Gly Leu Glu Trp Val Ser
        35                  40                  45

Arg Ile Ser Pro Gly Gly Asp Val Thr Trp Tyr Ala Asp Ser Val Lys
    50                  55                  60

Gly Arg Phe Thr Ile Ser Arg Asp Asn Ala Gln Asn Thr Leu Tyr Leu
65                  70                  75                  80

Gln Met Asn Ser Leu Arg Ala Glu Asp Thr Ala Val Tyr Phe Cys Ala
                85                  90                  95

Arg Asp Asp Ile Val Val Ser Arg Ile Phe Asp Asp Trp Gly Gln Gly
            100                 105                 110

Val Leu Leu Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Macaca fascicularis

<400> SEQUENCE: 2

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Ala Trp Tyr Gln Gln Lys Pro Gly Lys Ala Pro Lys Leu Leu Ile
        35                  40                  45

Tyr Asp Ala Ala His Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Val Tyr Tyr Cys Gln Gln Arg Asn Ser Tyr Pro Leu
                85                  90                  95

Thr Phe Gly Gly Gly Thr Lys Val Glu Ile Lys
            100                 105

<210> SEQ ID NO 3
<211> LENGTH: 13
<212> TYPE: PRT
<213> ORGANISM: Artificial Sequence
<220> FEATURE:
<223> OTHER INFORMATION: Macaca fascicularis

<400> SEQUENCE: 3

Ala Arg Asp Asp Ile Val Val Ser Arg Ile Phe Asp Asp
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Macaca fascicularis -continued

```
<400> SEQUENCE: 4

Gln Gln Arg Asn Ser Tyr Pro Leu Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Macaca fascicularis

<400> SEQUENCE: 5

Gly Phe Thr Phe Thr Asp Tyr Tyr
1               5

<210> SEQ ID NO 6
<211> LENGTH: 6
<212> TYPE: PRT
<213> ORGANISM: Artificial Sequence
<220> FEATURE:
<223> OTHER INFORMATION: Macaca fascicularis

<400> SEQUENCE: 6

Gln Ser Ile Arg Ser Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: Macaca fascicularis

<400> SEQUENCE: 7

Ile Ser Pro Gly Gly Asp Val Thr
1               5

<210> SEQ ID NO 8
<211> LENGTH: 3
<212> TYPE: PRT
<213> ORGANISM: Artificial Sequence
<220> FEATURE:
<223> OTHER INFORMATION: Macaca fascicularis

<400> SEQUENCE: 8

Asp Ala Ala
1

<210> SEQ ID NO 9
<211> LENGTH: 245
<212> TYPE: PRT
<213> ORGANISM: Artificial Sequence
<220> FEATURE:
<223> OTHER INFORMATION: Macaca fasicularis

<400> SEQUENCE: 9

Gln Val Gln Leu Leu Glu Ser Gly Gly Gly Leu Ala Lys Pro Gly Gly
1               5                   10                  15

Ser Leu Arg Leu Ser Cys Ala Ala Ser Gly Phe Thr Phe Thr Asp Tyr
                20                  25                  30

Tyr Met Asp Trp Val Arg Gln Ala Pro Gly Lys Gly Leu Glu Trp Val
            35                  40                  45

Ser Arg Ile Ser Pro Gly Gly Asp Val Thr Trp Tyr Ala Asp Ser Val
        50                  55                  60

Lys Gly Arg Phe Thr Ile Ser Arg Asp Asn Ala Gln Asn Thr Leu Tyr
```

-continued

```
65                  70                  75                  80
Leu Gln Met Asn Ser Leu Arg Ala Glu Asp Thr Ala Val Tyr Phe Cys
                85                  90                  95

Ala Arg Asp Asp Ile Val Val Ser Arg Ile Phe Asp Asp Trp Gly Gln
            100                 105                 110

Gly Val Leu Leu Thr Val Ser Ser Ala Ser Thr Lys Gly Pro Lys Leu
        115                 120                 125

Glu Glu Gly Glu Phe Ser Glu Ala Arg Val Glu Leu Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Ser Ile Arg Ser Tyr Leu Ala Trp Tyr Gln Gln
                165                 170                 175

Lys Pro Gly Lys Ala Pro Lys Leu Leu Ile Tyr Asp Ala Ala His Leu
            180                 185                 190

Gln Ser Gly Val Pro Ser Arg Phe Ser Gly Ser Gly Ser Gly Thr Glu
        195                 200                 205

Phe Ser Leu Thr Ile Ser Ser Leu Gln Pro Glu Asp Phe Ala Val Tyr
    210                 215                 220

Tyr Cys Gln Gln Arg Asn Ser Tyr Pro Leu Thr Phe Gly Gly Gly Thr
225                 230                 235                 240

Lys Val Glu Ile Lys
                245

<210> SEQ ID NO 10
<211> LENGTH: 18
<212> TYPE: PRT
<213> ORGANISM: Artificial Sequence
<220> FEATURE:
<223> OTHER INFORMATION: lien peptidique (peptide bond) artificial
      synthetic peptidic linker

<400> SEQUENCE: 10

Ala Ser Thr Lys Gly Pro Lys Leu Glu Glu Gly Glu Phe Ser Glu Ala
1               5                   10                  15

Arg Val
```